(12) United States Patent
Lee et al.

(10) Patent No.: US 8,511,312 B2
(45) Date of Patent: Aug. 20, 2013

(54) RESPIRATORY AUXILIARY DEVICE

(75) Inventors: Gary C. J. Lee, I-Lan (TW); Shu-Ping Zou, Taipei (TW); Yi-He Lee, Taipei (TW)

(73) Assignee: Galemed Corporation, I-Lan (TW)

( * ) Notice: Subject to any disclaimer, the term of this patent is extended or adjusted under 35 U.S.C. 154(b) by 925 days.

(21) Appl. No.: 12/493,413

(22) Filed: Jun. 29, 2009

(65) Prior Publication Data

US 2010/0000545 A1    Jan. 7, 2010

(30) Foreign Application Priority Data

Jul. 2, 2008   (TW) ................................ 97211749 U (51) Int. Cl.

| | | |
|---|---|---|
| *A61M 15/08* | (2006.01) | |
| *A61M 16/00* | (2006.01) | |
| *A62B 7/00* | (2006.01) | |
| *A62B 18/08* | (2006.01) | |
| *A62B 7/10* | (2006.01) | |
| *A62B 23/02* | (2006.01) | |
| *A61G 10/00* | (2006.01) | |

(52) U.S. Cl.
USPC ............ 128/207.18; 128/203.22; 128/206.11; 128/207.11

(58) Field of Classification Search
USPC ............ 128/200.24, 200.26, 203.22, 206.11, 128/207.13, 207.18
See application file for complete search history.

(56) References Cited

U.S. PATENT DOCUMENTS

| | | | | |
|---|---|---|---|---|
| 4,485,822 | A * | 12/1984 | O'Connor et al. ............ 600/532 |
| 4,774,946 | A * | 10/1988 | Ackerman et al. ....... 128/207.18 |
| 5,400,781 | A * | 3/1995 | Davenport ............... 128/206.28 |
| 5,617,847 | A * | 4/1997 | Howe ....................... 128/204.23 |
| 7,066,180 | B2 * | 6/2006 | Aylsworth et al. ....... 128/207.18 |
| 2006/0112957 | A1 * | 6/2006 | Johnson ................... 128/201.11 |
| 2008/0099012 | A1 * | 5/2008 | Johnson ................... 128/201.11 |
| 2011/0094518 | A1 * | 4/2011 | Cipollone et al. ....... 128/207.18 |

* cited by examiner

*Primary Examiner* — Oren Ginsberg
(74) *Attorney, Agent, or Firm* — Duane Morris LLP (57) ABSTRACT

A respiratory auxiliary device includes a first conduit provided with a pair of nasal prongs and having two opposite end portions, two second conduits connected fluidly and respectively to the end portions, and a pressure-measuring pipe adapted for connection with a pressure-measuring device. One of the second conduits is adapted for discharging air exhaled by a patient. The other one of the second conduits is adapted to be connected to an air supply device. The pressure-measuring pipe is disposed within said one of the second conduits, and has one end extending into the first conduit in proximity to the nasal prongs.

6 Claims, 7 Drawing Sheets

RESPIRATORY AUXILIARY DEVICE

CROSS-REFERENCE TO RELATED APPLICATION

This application claims priority of Taiwanese Application No. 097211749, filed on Jul. 2, 2008.

BACKGROUND OF THE INVENTION

1. Field of the Invention

This invention relates to an improved respiratory auxiliary device.

2. Description of the Related Art

Figure 1:
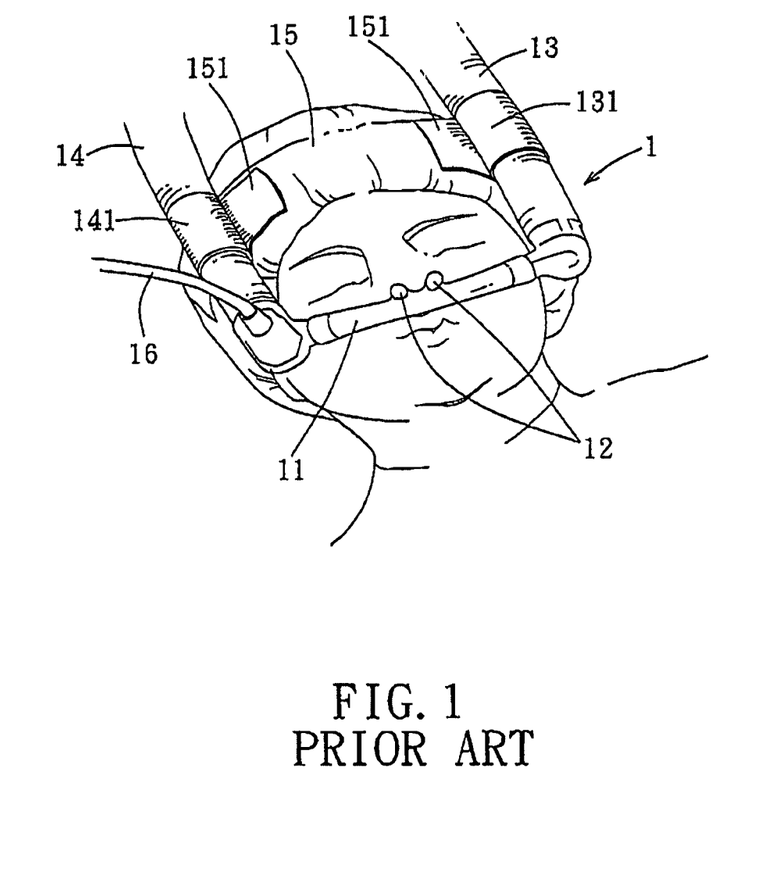
FIG. 1 is a schematic view of a conventional oxygen delivery device in a state of use.

Referring to FIG. 1, a conventional respiratory auxiliary device 1 includes a first conduit 11, a pair of nasal prongs 12 projecting from and communicating fluidly with the first conduit 11, two second conduits 13, 14 connected respectively to two opposite ends of the first conduit 11, a headgear unit 15 placed onto the head of a patient, for example a small child or infant, and a pressure-measuring pipe 16. The second conduits 13, 14 are connected respectively to an air inlet and an air outlet of an air supply device (not shown). The nasal prongs 12 are disposed toward the patient's nostrils. Air flows into the patient's nostrils through the nasal prongs 12 for inhalation by the patient. The pressure-measuring pipe 16 has one end disposed in the first conduit 11, and the other end connected to a pressure-measuring device (not shown) so as to determine whether the airflow pressure and the concentration of carbon dioxide gas inside the tubes of the conventional respiratory auxiliary device 1 are maintained at normal levels. The headgear unit 15 has a looped marginal end provided with two spaced-apart loop fasteners 151 at two opposite sides thereof. Two hook fasteners 131, 141 are sleeved respectively on the second conduits 13, 14 to engage respectively the loop fasteners 151. Through inter-engagement of the hook and loop fasteners 131, 141, 151, the second conduits 13, 14 can be positioned respectively on two opposite sides of the head of the patient. Since the hook fasteners 131, 141 are sleeved respectively on the second conduits 13, 14, they easily move upwardly and downwardly along the respective second conduits 13, 14 when the patient turns his/her head. Further, since the pressure-measuring pipe 16 is exposed, it is easily entangled around the second conduit 14. Moreover, since the first conduit 11 is made of silicone and has a smooth outer surface, such that the first conduit 11 easily presses against the philtrum of the patient, and is adhered thereto. This can bring discomfort to the patient, even resulting in injury to the skin of the patient, as well as suppressing the growth of facial skin tissues of the patient. This is particularly the case when the patient is a small child or infant.

SUMMARY OF THE INVENTION

Therefore, the object of the present invention is to provide a respiratory auxiliary device that is capable of overcoming the aforementioned drawbacks of the prior art.

According to one aspect of this invention, a respiratory auxiliary device comprises a first conduit provided with a pair of nasal prongs and having two opposite end portions, two second conduits connected fluidly and respectively to the end portions, and a pressure-measuring pipe adapted for connection with a pressure-measuring device. One of the second conduits is adapted for discharging air exhaled by a patient. The other one of the second conduits is adapted to be connected to an air supply device. The pressure-measuring pipe is disposed within said one of the second conduits, and has one end extending into the first conduit in proximity to the nasal prongs.

According to another aspect of this invention, a respiratory auxiliary device comprises a first conduit and two second conduits The first conduit includes two opposite end portions, an intermediate portion between the end portions, and a pair of nasal prongs provided on the intermediate portion. The intermediate portion has a tubular wall with a cross section resembling the shape of a segment so that the tubular wall has a chordal wall section that is flat in a chordal direction, and an arc-shaped wall section opposite to the chordal wall section. The chordal wall section extends axially between the end portions, and is concaved gradually from the end portions to a midpart of the chordal wall section so that the chordal wall section does not pressurize the philtrum of a patient. The nasal prongs project outwardly from the arc-shaped wall section. The second conduits are connected fluidly and respectively to the end portions.

According to still another aspect of this invention, a respiratory auxiliary device comprises a first conduit provided with a pair of nasal prongs and having two opposite end portions, two second conduits connected fluidly and respectively to the end portions, and a fixing unit including a head accessory for being placed onto the head of a patient, a support frame which includes a plate body positioned removably on the head accessory, and a C-shaped clamp projecting outwardly from one side of the plate body to clamp the one of the second conduits, and a positioning member to position removably the plate body on the head accessory.

BRIEF DESCRIPTION OF THE DRAWINGS

Other features and advantages of the present invention will become apparent in the following detailed description of the preferred embodiment of the invention, with reference to the accompanying drawings, in which.

DETAILED DESCRIPTION OF THE PREFERRED EMBODIMENT

Referring to FIGS. 2 to 10, a respiratory auxiliary device 2 according to the preferred embodiment of the present invention is shown to comprise a first conduit 21, two second conduits 22, and a fixing unit 24.

Figure 3:
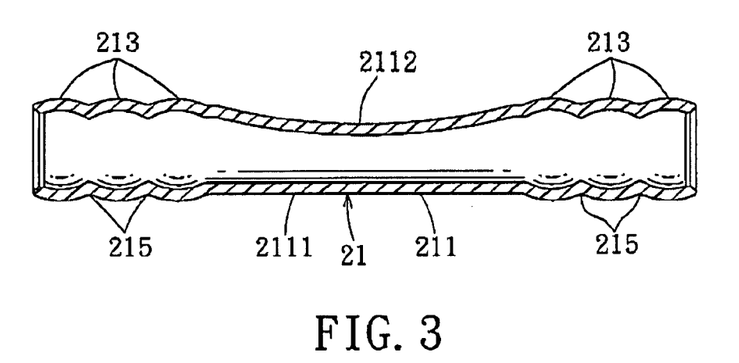
FIG. 3 is a sectional top view of a first conduit of the preferred embodiment, illustrating each end of the first conduit having a plurality of first annular bulges.
Figure 4:
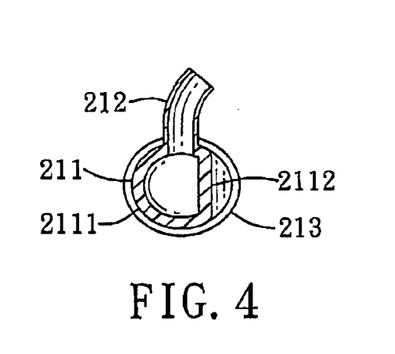
FIG. 4 is a sectional side view of the first conduit.
Figure 5:
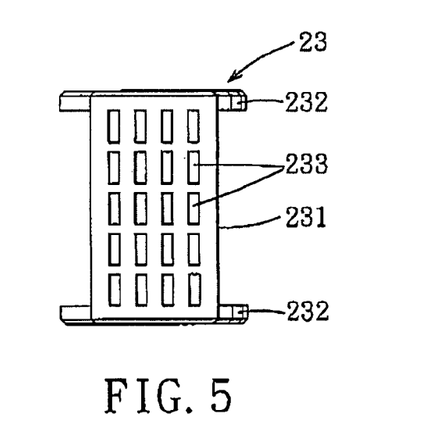
FIG. 5 is a schematic view of a support frame of the preferred embodiment.
Figure 6:
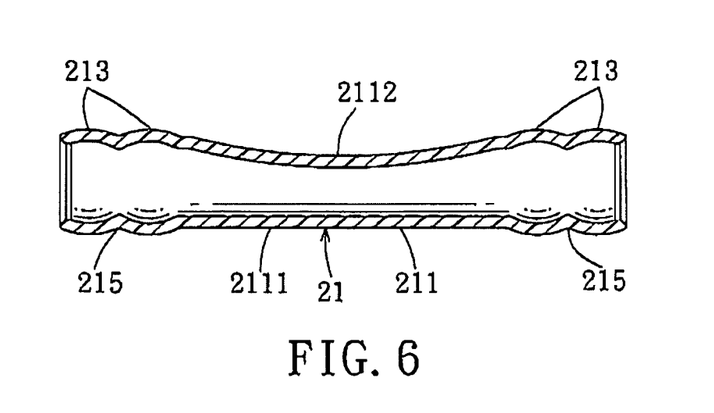
FIG. 6 is a view similar to FIG. 3, but illustrating the first conduit in a state in which an outermost annular bulge at each end thereof has been cut off through a valley formed between the outermost annular bulge and an adjacent one of the annular bulges.

The first conduit 21 is made of a resilient material, and has left and right end portions 210, and an intermediate portion 211 between the left and right end portions 210. Each of the left and right end portions 210 has a plurality of first annular bulges 213 of arc-shaped cross section, and a plurality of valleys 215 each formed between two adjacent ones of the first annular bulges 213. Each valley 215 can be used as a reference for cutting off at least one of the first annular bulges 213 at each of the left and right end portions 210 of the first conduit 21, so that the length of the first conduit 21 can be adjusted to suit a patient. The intermediate portion 211 has a tubular wall with a cross section resembling the shape of a segment so that the tubular wall has a chordal wall section 2112 that is flat in a chordal direction, and an arc-shaped wall section 2111 opposite to the chordal wall section 2112. The chordal wall section 2112 extends axially between the left and right end portions 210, and is concaved gradually from the left and right end portions 210 to a midpart of the chordal wall section 2112 so that the chordal wall section 2112 does not pressurize the philtrum of a patient. A pair of nasal prongs 212 projects upwardly from the arc-shaped wall section 2111, and is adapted to be inserted into the nostrils of the patient. The arc-shaped wall section 2111 has a concaved surface 214 formed between the nasal prongs 212, and is adapted to abut against a bottom of the nose of the patient.

Figure 2:
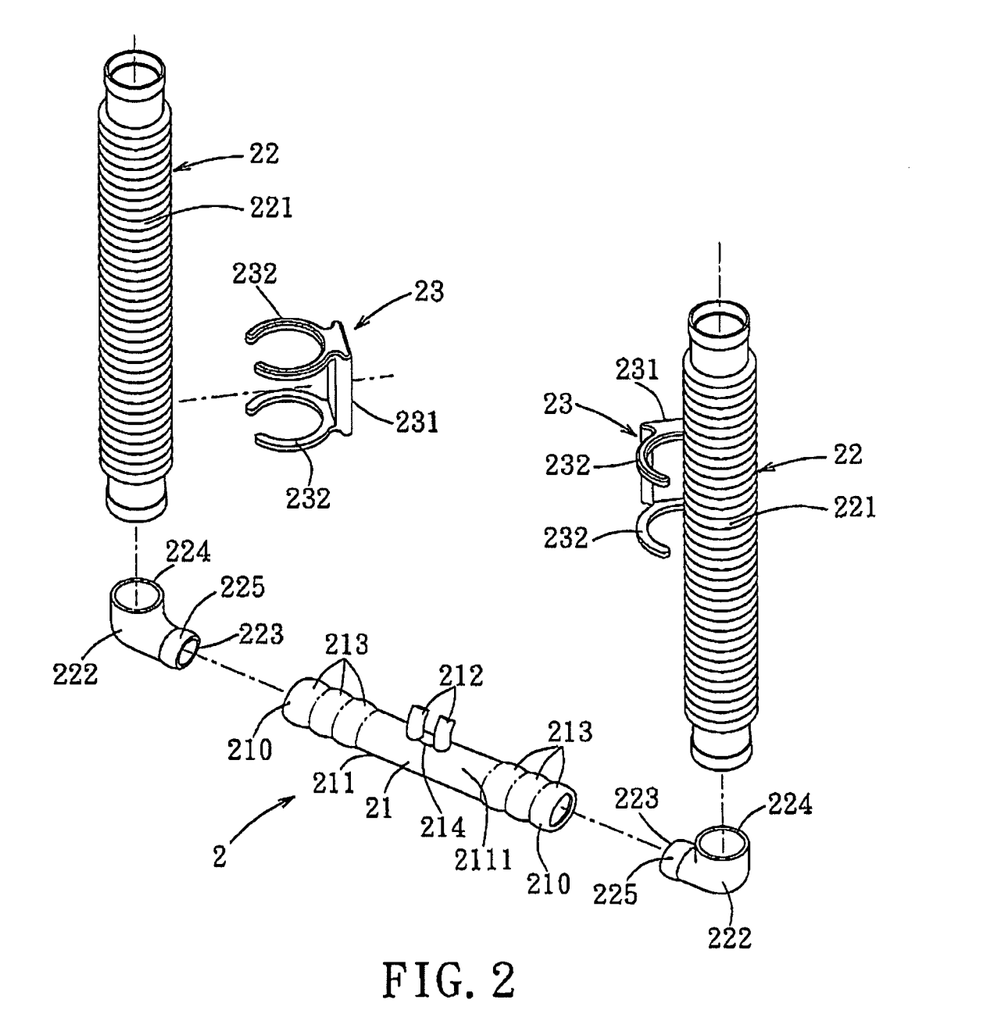
FIG. 2 is an exploded perspective view of a respiratory auxiliary device according to the preferred embodiment of this invention.

Each of the second conduits 22 includes a corrugated tube 221, and a connecting tube 222 connected to a bottom end of the corrugated tube 221 and one of the left and right end portions 210 of the first conduit 21. The connecting tube 222 is angled into a substantially L-shaped configuration, and has a first end 223 formed with a second annular bulge 225 that mates rotatably with an outermost first annular bulge 213 at one of the left or right end portion of the first conduit 21, and a second end 224 opposite to the first end 223 and connected fluidly to the bottom end of the corrugated tube 221. It should be noted that the first ends 223 of the connecting tubes 222 are configured to form the second annular bulges 225, respectively, that mate rotatably with the outermost first annular bulges 213 at the respective left and right end portions 210 of the first conduit 21, so that angular adjustment of the second conduits 22 relative to the first conduit 21 can be achieved.

The fixing unit 24 includes two support frames 23, each of which includes a plate body 231, and two spaced-apart C-shaped clamps 232 that extend outwardly and respectively from top and bottom ends of the plate body 231 and that are disposed on a same one side of the plate body 231 to clamp the corrugated tube 221 of one of the second conduits 22. The other side of the plate body 231 is formed with an array of grooves 233 (see FIG. 5), the purpose of which is not only to minimize the amount of material needed for the plate body 231, but also to reduce frictional contact between the other side of the plate body 231 and a positioning surface of another component of the fixing unit 24, i.e., a head accessory 241 which will be described later in the description, and the static force. It should be noted that, with reference to FIG. 9, when the C-shaped clamps 232 of each support frame 23 are clamped onto the corrugated tube 221 of the corresponding second conduit 22, a gap 234 is formed between the plate body 231 of the support frame 23 and the corrugated tube 221 of the corresponding second conduit 22.

Figure 7:
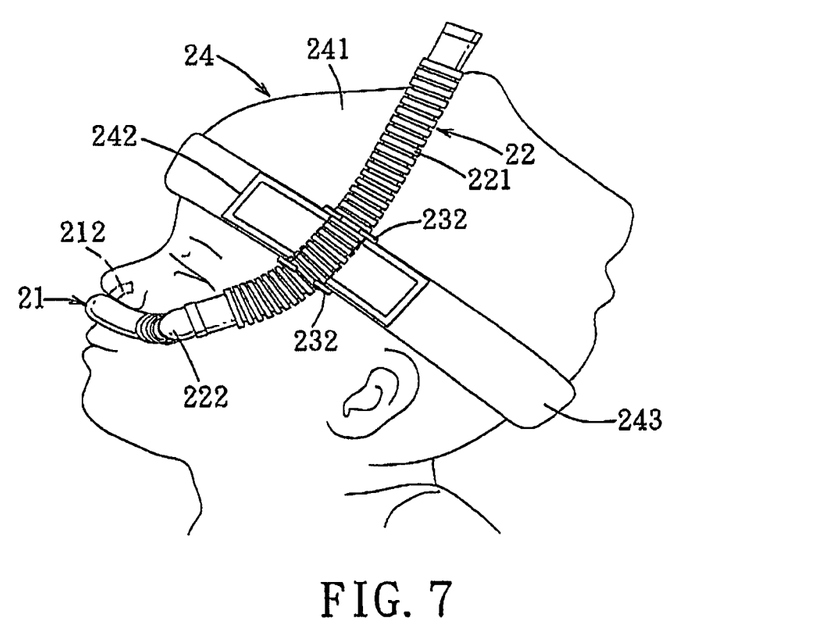
FIG. 7 is a perspective view of the preferred embodiment in a state of use.
Figure 8:
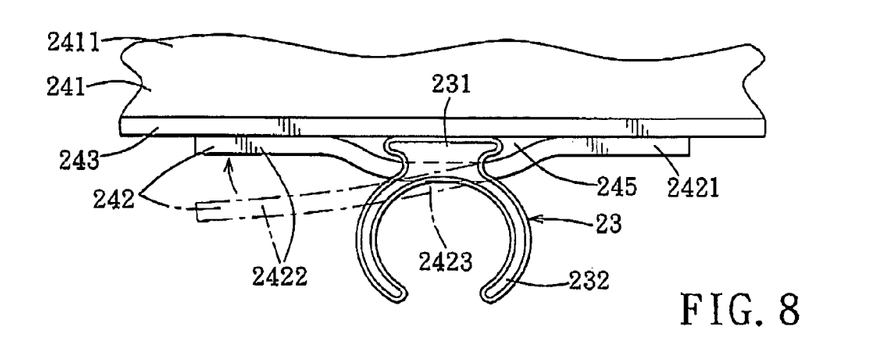
FIG. 8 is a fragmentary schematic view of the preferred embodiment, illustrating how the support frame is positioned on a head accessory of the preferred embodiment.

As shown in FIGS. 7 and 8, the fixing unit 24 further includes a head accessory 241, and two positioning members 242 (only one is visible in FIG. 7) disposed respectively on two opposite sides of the head accessory 241. The head accessory 241 is configured as headgear that is placed onto the head of the patient, and is made of a fabric material to enhance the degree of comfort during use of the head accessory or headgear 241. An elastic band may be provided on a looped marginal end 243 of the headgear 241 to accommodate different patient head sizes. In this embodiment, each of the positioning members 242 has a strap with two connecting ends 2421, 2422, and a mid-portion 2423 between the connecting ends 2421, 2422. The connecting end 2421 is fixed to the looped marginal end 243. The connecting end 2422 is connected releasably to the looped marginal end 243 through hook and loop fasteners (not shown) provided respectively on the connecting end 2422 and the looped marginal end 243 of the headgear 241. The mid-portion 2423 extends into the gap 234 (see FIG. 9) so as to confine the plate body 231 of the support frame 23 within a receiving space 245 cooperatively defined by the mid-portion 2423 and the looped marginal end 243 of the headgear 241.

Figure 9:
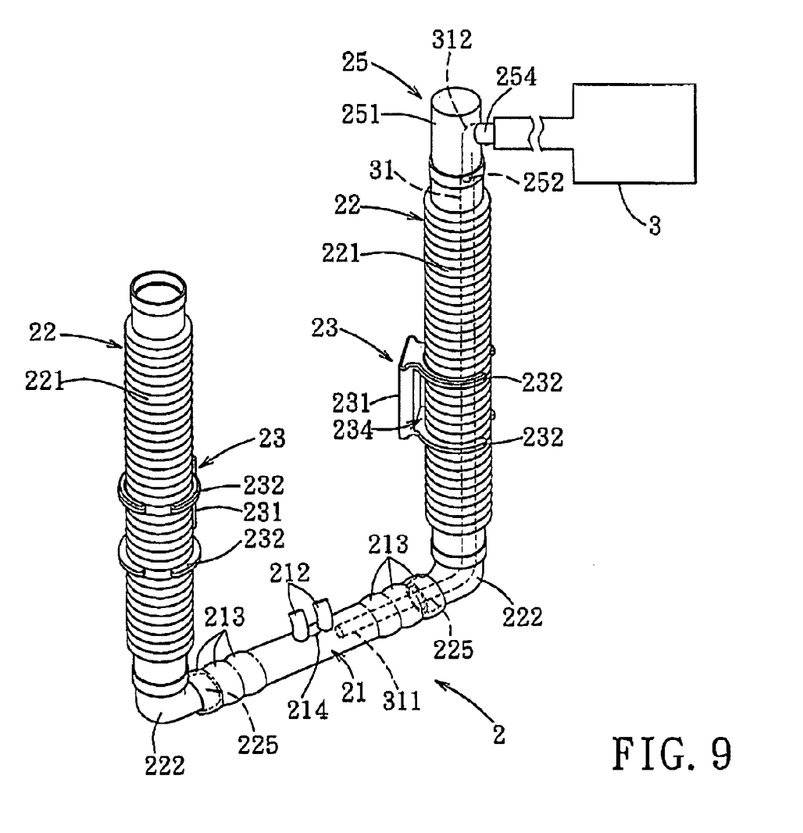
FIG. 9 is a perspective view of the preferred embodiment in an assembled state.

The respiratory auxiliary device 2 of the present invention is particularly suitable for use on a small child or infant, but is not limited thereto. After assembly of the first conduit 21, the corrugated tubes 221 and the connecting tubes 222 of the second conduits 22, and the support frames 23 so as to form an integral body, as best shown in FIG. 9, the headgear 241 is then placed onto the head of a small child, as best shown in FIG. 7. The nasal prongs 212 are inserted into the nostrils of the small child with the concaved surface 214 abutting against the bottom of the nose of the small child. It should be noted that the presence of the concaved surface 214 between the nasal prongs 212 prevents the first conduit 21 from pressing against the nasal septum of the nose of the small child which could make the small child uncomfortable. The corrugated tubes 221 of the second conduits 22 extend respectively on two opposite sides of the head of the small child. The connecting end 2422 of each positioning member 242 passes through the gap 234, and engages releasably the looped marginal end 243 of the headgear 241, thereby quickly mounting the assembly of the first conduit 21, the corrugated tubes 221 and the connecting tubes 222 of the second conduits 22, and the support frames 23 to the head of the small child.

In this embodiment, the second conduit 22 that is connected to the left end portion 210 of the first conduit 21 (or the "left second conduit 22") is adapted to be connected to an air supply device (not shown) for supply of air to be inhaled by the small child via the first conduit 21 and the nasal prongs 212, and the second conduit 22 that is connected to the right end portion 210 of the first conduit 21 (or the "right second conduit 22") is adapted for discharging air exhaled by the small child and the excess air in the first conduit 21.

Figure 10:
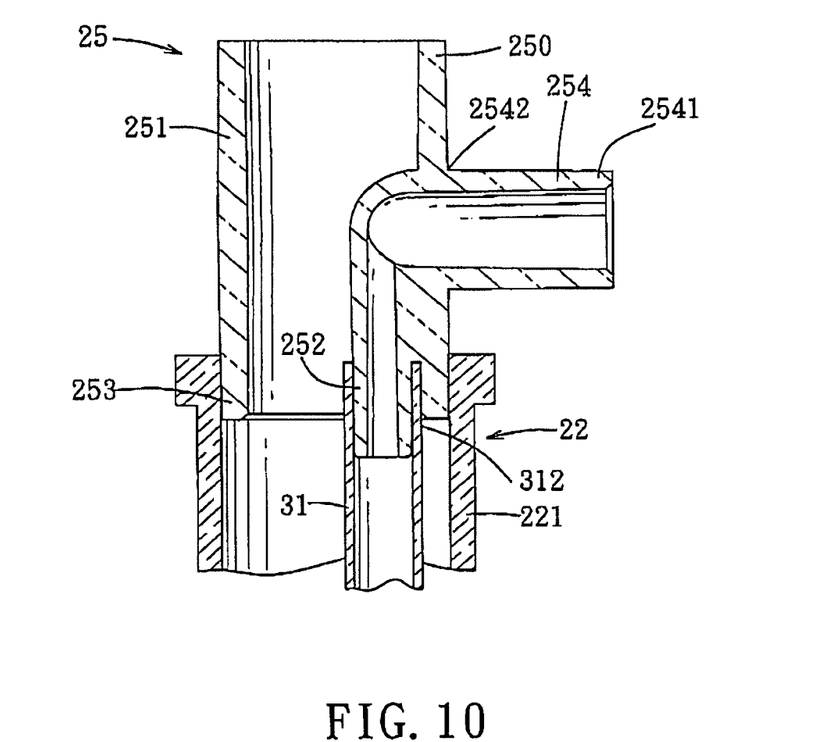
FIG. 10 is an enlarged sectional view of a T-shaped connector of the preferred embodiment.

With reference to FIGS. 9 and 10, to determine whether the airflow pressure and the concentration of carbon dioxide gas inside the tubes of the respiratory auxiliary device 2 are maintained at normal levels, a pressure-measuring device 3 may be connected to the right second conduit 22. Since the pressure-measuring device 3 is known in the art, a detailed description of the same is dispensed herewith. A pressure-measuring pipe 31 is disposed within the right second conduit 22, and has one end 311 extending into the first conduit 21 in proximity to the nasal prongs 212. The respiratory auxiliary device 2 further comprises a T-shaped connector 25 having a main tube 251 connected fluidly to the right second conduit 22, and a side tube 254 projecting transversely from the main tube 251. The main tube 251 has one end 253 connected to a top end of the corrugated tube 221 of the right second conduit 22, and the other end 250 opposite to the end 253 in an axial direction for discharging of air. The side tube 254 has an outer end 2541 adapted to be connected with the pressure-measuring device 3, and an inner end 2542 connected to the main tube 251. The T-shaped connector 25 further has an inner tube 252 disposed within the main tube 251, connected integrally to the inner end 2542 of the side tube 254, and bending from the inner end 2542 of the side tube 254 into the main tube 251 and partially out of the end 253 of the main tube 251 so as to connect with the other end 312 of the pressure-measuring pipe 31. Hence, the pressure-measuring pipe 31 is disposed stably within the right second conduit 22 through the T-shaped connector 25. This prevents the pressure-measuring pipe 31 from being entangled around the right second conduit 22, which could if the pressure-measuring pipe 31 was disposed externally of the right second conduit 22. Further, the end 311 of the pressure-measuring pipe 31 can be disposed closer to the nasal prongs 212, so that, in comparison with a conventional pressure-measuring method, the airflow pressure and the concentration of the carbon dioxide gas inside the tubes of the respiratory auxiliary device 2 can be measured more accurately. Moreover, the bottom end of the corrugated tube 221 of the right second conduit 22 may be provided with a pressure valve (not shown) for adjusting suitably the pressure inside the tubes of the respiratory auxiliary device 2, thereby effectively preventing the formation of inappropriate pressure inside the tubes of the respiratory auxiliary device 2 which could bring discomfort to the small child during breathing.

Since the first conduit 21 is made of a resilient material, and since the chordal wall section 2112 is concaved, the first conduit 21 is prevented from pressing against the philtrum of the small child and from suppressing the growth of facial skin tissues of the small child. Hence, the concave configuration of the chordal wall section 2112 does not inhibit the growth of facial skin tissues of the small child or infant. Moreover, because the chordal wall section 2112 is concaved, the position of the first conduit 21 can be fixed and the first conduit 21 can be prevented from turning due to an external force. Additionally, an outer surface of the chordal wall section 2112 has a matte finish surface, so that the outer surface of the chordal wall section 2112 is not slippery. As a result, the outer surface of the chordal wall section 2112 will not adhere to the skin of the small child or infant, which could hurt or injure the skin of the small child or infant.

Figure 11:
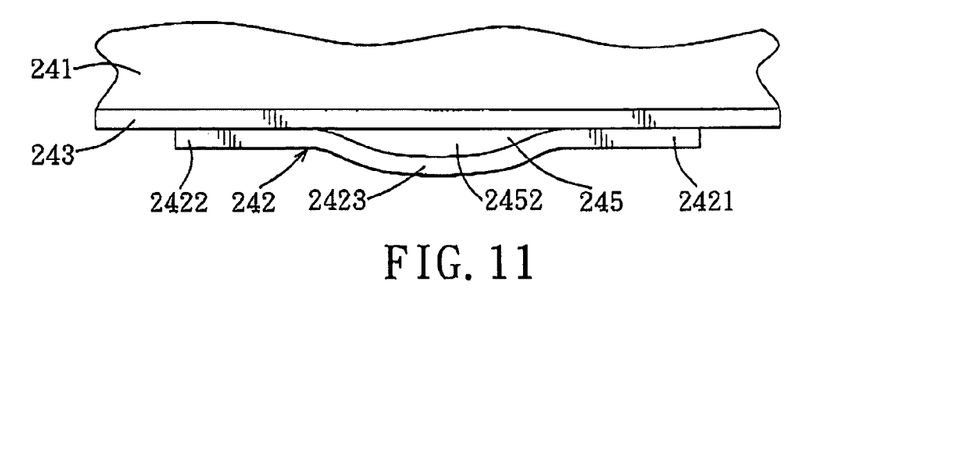
FIG. 11 illustrates an alternative form of a positioning member of a fixing unit of the preferred embodiment.
Figure 12:
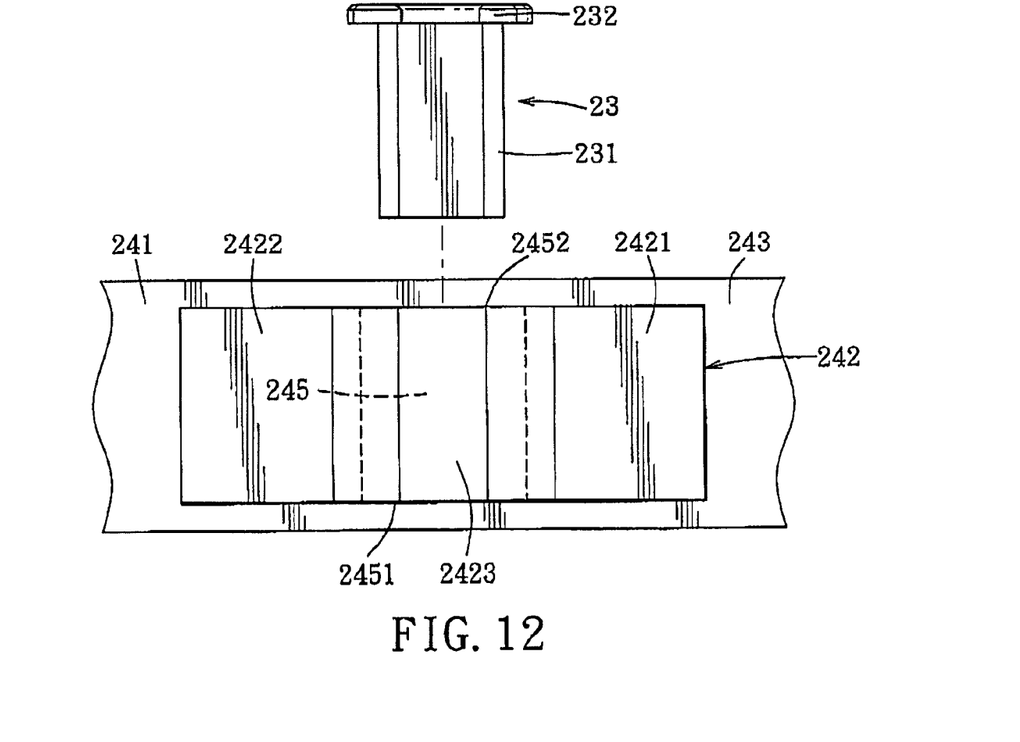
FIG. 12 illustrates an alternative form of a support frame of the preferred embodiment in a state of being connected to the positioning member of FIG. 11.

Referring to FIGS. 11 and 12, the two connecting ends 2421, 2422 of the positioning member 242, in an alternative embodiment, may be sewn to the looped marginal end 243 of the headgear 241, and the mid-portion 2423 has one end sewn to the looped marginal end 243 so that the receiving space 245 has a closed end 2451 and an open end 2452. Further, the support frame 23 may be provided with only one C-shaped clamp 232 that extends outwardly from the top end of the plate body 2311 of the support frame 23. Through such a configuration, the plate body 2311 may be inserted into the receiving space 245 via the open end 2452. Hence, the support frame 23 can be similarly and easily positioned on the positioning member 242.

In another alternative embodiment, the side of the plate body of each support frame 23 (see FIG. 2) that is opposite to the C-shaped clamps may be provided with a hook fastener (not shown), and the looped marginal end 243 (see FIG. 7) of the headgear may be provided with a loop fastener (not shown), so that the plate body of each support frame 23 may be directly connected to the looped marginal end 243 of the headgear through the hook and loop fasteners. Hence, the positioning member 242 may be dispensed herewith.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

We claim:

1. A respiratory auxiliary device comprising:
    a first conduit provided with a pair of nasal prongs and having two opposite end portions;
    two second conduits each having one end connected to a respective one of said end portions of said first conduit, and the other end distal from said first conduit, one of said second conduits being adapted for discharging air exhaled by a patient, the other one of said second conduits being adapted to be connected to an air supply device; and
    a pressure-measuring pipe adapted for connection with a pressure-measuring device, said pressure-measuring pipe being entirely disposed within said one of said second conduits and said first conduit, said pressure-measuring pipe having one end extending into said first conduit in proximity to said nasal prongs, and the other end proximate to said other end of said one of said second conduits.

2. The respiratory auxiliary device of claim 1, further comprising a fixing unit that includes a head accessory for being placed onto the head of a patient, a support frame to hold one of said second conduits, and a positioning member provided on said head accessory, said support frame being positioned removably on said head accessory through said positioning member.

3. The respiratory auxiliary device of claim 1, further comprising a T-shaped connector having a main tube, and a side tube projecting transversely from said main tube, said main tube having one end connected fluidly to said one of said second conduits, said side tube having an outer end adapted to be connected with the pressure-measuring device, and an inner end connected to said main tube, said T-shaped connector further having an inner tube disposed within said main tube and connected to said inner end of said side tube and said pressure-measuring pipe.

4. A respiratory auxiliary device of claim 1, further comprising:
    a fixing unit that includes a head accessory for being placed onto the head of a patient, a support frame which includes a plate body positioned removably on said head accessory, and a C-shaped clamp projecting outwardly from one side of said plate body to clamp said one of said second conduits, and a positioning member to position removably said plate body on said head accessory.

5. The respiratory auxiliary device of claim 4, wherein said head accessory is made of a fabric material, said positioning member having a strap with two connecting ends connected to said head accessory, and a mid-portion cooperating with said head accessory to define a receiving space to receive said plate body of said support frame.

6. The respiratory auxiliary device of claim 4, wherein said head accessory is configured as headgear.

* * * * *